US00PP08643P

United States Patent [19]

Neuroth

[11] Patent Number: Plant 8,643

[45] Date of Patent: Mar. 15, 1994

[54] ALSTROEMERIA PLANT NAMED INCA KOYA

[76] Inventor: Michael R. Neuroth, 2322 N. Nugent Rd., Lummi Island, Wash. 98202

[21] Appl. No.: 929,820

[22] Filed: Aug. 14, 1992

[51] Int. Cl.[5] ..... A01H 5/00

[52] U.S. Cl. ..... Plt./87.1

[58] Field of Search ..... Plt. 87.1

*Primary Examiner*—James R. Feyrer

*Assistant Examiner*—Bruce R. Campell

*Attorney, Agent, or Firm*—Chernoff, Vilhauer, McClung and Stenzel

[57] ABSTRACT

A new and distinct variety of Alstroemeria distinguished by its mildly spicy carnation fragrance and rose-pink flowers highlighted by the white central portion of the inner petals, the upper portions of which are tipped in rose-pink. Brown streaks are present on the inner petals increasing in size toward the outer end of the petals.

1 Drawing Sheet

BACKGROUND OF THE NEW PLANT

The present invention comprises a new and distinct cultivar of Alstroemeria plant, known by the cultivar name Inca Koya, originiated by the inventor Michael Neuroth from a hybridization made in a controlled breeding program on Lummi Island, Wash., U.S.A., in August 1990. The female parent being the Brazilian specie *A. caryophyllae* and the male pollen parent being of unknown parentage but of select quality.

The new cultivar was selected as one flowering plant within the progeny of the stated parentage by Michael Neuroth on Jul. 30, 1991 in a controlled environment on Lummi Island, Wash.

The first asexual reproduction of the new cultivar was done by rhizome divisions taken from the initial selection on Nov. 29, 1991 in a controlled environment on Lummi Island by Michael Neuroth. Examination of plants reproduced by the above rhizome division has demonstrated that the combination of characteristics as herein disclosed and claimed for the new cultivar are firmly fixed and retained through generations of asexual reproduction.

The new cultivar has not been observed under all possible environmental conditions. The phenotype may vary with changes in environment such as temperature, light intensity and day length. The following observations, measurements and comparisons describe plants grown on Lummi Island under greenhouse conditions which approximate those generally used in commercial practice.

The following traits have been repeatedly observed and are determined to be basic characteristics of the new cultivar which together distinguish this Alstroemeria as a new and distinct cultivar:

1. Medium flowers with the outer perigon petals being rose-pink and the inner perigon petals being cream white tipped in rose-pink.
2. Streaking appears on the upper surface of the inner perigon petals, with streaks being dark brown and increasing in thickness towards the outer ends of these inner petals.
3. Long or short stems depending on temperature and light intensity.
4. Long flowering season.
5. Fragrant flowers.

DESCRIPTION OF THE DRAWING

This new Alstroemeria cultivar is illustrated by the accompanying photographic drawing which shows face views of a number of the flowers comprising an umbel cluster, the color rendition being as nearly true to those specified herein as is possible to obtain by conventional photographic procedures.

DESCRIPTION OF THE NEW PLANT

Figure 1:
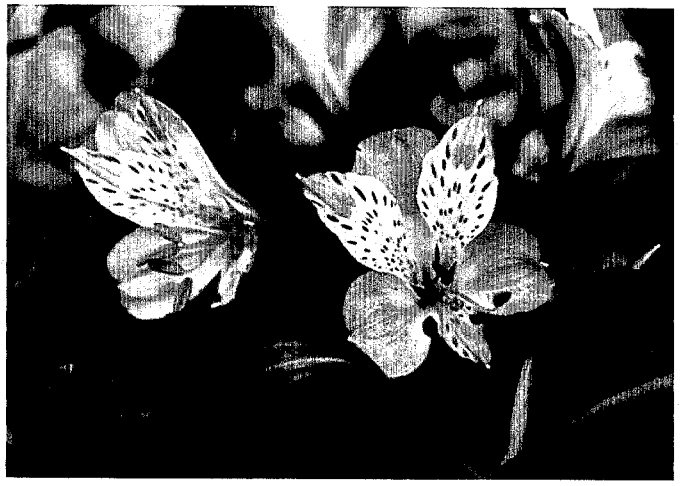
Figure 2:
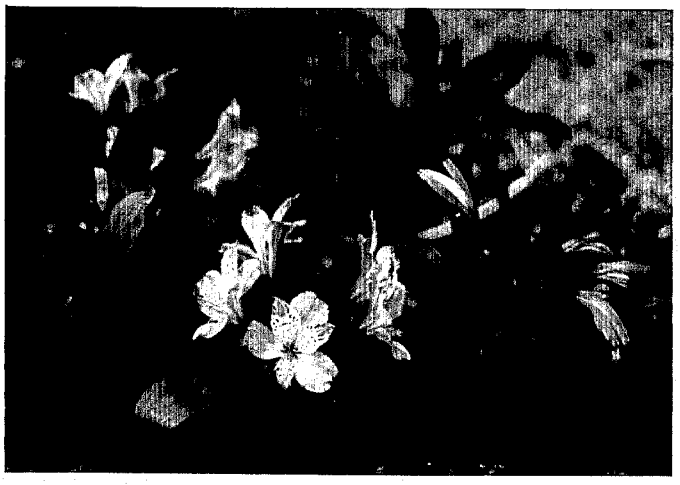

In the following description, wherever possible, color references are made to The Royal Horticultural Society Colour Chart. The color values were determined in the afternoon of Mar. 27, 1992 under natural light at Bellingham, Wash., U.S.A.

PLANT

Origin: Seedling.

Parentage: *xAlstroemeria caryophyllae* xselect hybrid (unknown origin).

Form: Erect bush.

Height: Varying with the seasons-light intensity and temperature; between 12"-30" with each blooming cane varying in length between those heights.

Branching: None.

Growth habit: Fast growing with vigorous, upright stems.

Foliage:

*Quantity.*—Moderate.

*Leaf size.*—10 to 14 cm long; 3 to 3.5 cm wide.

*Leaf shape.*—Elliptical with entire margins.

*Texture.*—Leathery.

*Color.*—Upper side — Glossy Green. Under side — Medium Green.

Rhizomes:

*Color.*—White.

*Size.*—Normal.

BUD

Size: Medium.

*Diameter.*—About 1.5 cm.

*Length.*—About 3 cm.

Form: Pear shaped.

Opening rate: Normal.

Sepals:

*Number.*—Six.

*Shape.*—Elliptical.
*Color of petals.*—54-B.
Flower stem:
*Length.*—between 4 and 8 cm, depending on season and growing conditions.
*Character.*—Strong and erect.

INFLORESCENCE

Blooming habit: Continuous year round.
Size of flower: Large.
*Diameter.*—About 5.5 cm.
*Depth.*—About 6 cm.
Borne: Singly on a stem of an umbel cluster of three to seven flowers, averaging about five.
Shape: Funnel-shaped with petal tips curling outwardly.
Scent: Fragrance similar to the scent of a mild spicy carnation.
Petalage:
*Number of petals.*—Six.
*Arrangement.*—Two concentric circles of 3 petals each.
*Texture.*—Leathery.
*Appearance.*—Shiny.
*Color.*—Outer petals: Body, Rose-pink 54-B; base portion, 55-B, reverse side, Rose-pink 54-B; outer petals are often, but not always, marked on the margins with light pencil stripes. Inner petals: white with the tip portion Rose-pink 54-B; inner petals are lightly covered with light pencil stripes extending longitudinally. Discoloration: after full bloom the petal coloration tends to run toward light pink.

*Flower stem length.*—About 4–5 cm.
Persistence: Flower petals stay on the stem for approximately two weeks after becoming fully open.
Lasting qualty:
*On the plant.*—About three weeks;
*As a cut flower.*—About two weeks.

REPRODUCTIVE ORGANS

Stamens:
*Number.*—Six.
*Arrangement.*—One opposite each petal.
*Anthers.*—Size: about 6 mm. Color: Cinnamon Grey.
*Filament length.*—About 3 cm.
*Color.*—54B.
*Pollen color.*—Cinnamon Grey.
Pistils
*Number.*—One.
*Style/length.*—About 3.5 cm.
*Color.*—54-B.
*Stigma color.*—54-B.

FRUIT

Fertility: The fruit is sterile.
Shape: Capsular.

What is claimed is:

1. The new and distinctive Alstroemeria cultivar, substantially as herein shown and described, characterized by the generally Rose-pink coloration of its large blossoms and distinguished in particular by the fragrance similar to the scent of a mildy spicy carnation.

* * * * *